US011491352B2

(12) United States Patent
Pahk et al.

(10) Patent No.: US 11,491,352 B2
(45) Date of Patent: Nov. 8, 2022

(54) HIGH-LOW INTENSITY FOCUSED ULTRASOUND TREATMENT APPARATUS

(71) Applicant: KOREA INSTITUTE OF SCIENCE AND TECHNOLOGY, Seoul (KR)

(72) Inventors: Ki Joo Pahk, Seoul (KR); Hyung Min Kim, Seoul (KR); Byung Chul Lee, Seoul (KR); Inchan Youn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 210 days.

(21) Appl. No.: 16/431,543

(22) Filed: Jun. 4, 2019

(65) Prior Publication Data
US 2019/0366126 A1 Dec. 5, 2019

(30) Foreign Application Priority Data
Jun. 5, 2018 (KR) .......................... 10-2018-0064719

(51) Int. Cl.
*A61N 7/00* (2006.01)
*A61B 8/00* (2006.01)
(Continued)

(52) U.S. Cl.
CPC ................ *A61N 7/00* (2013.01); *A61B 8/085* (2013.01); *A61B 8/0808* (2013.01);
(Continued)

(58) Field of Classification Search
CPC .......... A61N 7/00; A61N 7/02; A61B 8/0808; A61B 8/085; A61B 8/4494; A61B 8/461; A61B 8/54; A61B 8/0816
See application file for complete search history.

(56) References Cited

U.S. PATENT DOCUMENTS 5,471,988 A * 12/1995 Fujio ........................ A61B 8/12
600/439
5,769,790 A * 6/1998 Watkins ................... A61B 8/08
600/439
(Continued)

FOREIGN PATENT DOCUMENTS

CN 101623203 A * 1/2010
EP 3100767 A1 12/2016
(Continued)

OTHER PUBLICATIONS

R. Feng, et al., "Enhancement of ultrasonic cavitation yield by multi-frequency sonication," Ultrasonics Sonochemistry, vol. 9, pp. 231-236, Feb. 2002 (Year: 2002).*
(Continued)

*Primary Examiner* — Oommen Jacob
*Assistant Examiner* — Nyrobi Celestine
(74) *Attorney, Agent, or Firm* — Birch, Stewart, Kolasch & Birch, LLP

(57) ABSTRACT

A high-low intensity focused ultrasound treatment apparatus according to the present disclosure includes a plurality of ultrasound sources, and a controller to control a center frequency and intensity of focused ultrasound outputted from the ultrasound sources, wherein each of the ultrasound sources includes a first ultrasound transducer to output low-intensity focused ultrasound to detect a lesion, and a second ultrasound transducer to output high-intensity focused ultrasound to ablate or remove the detected lesion. The low-intensity focused ultrasound outputted from the first transducer may be used to detect a lesion in a patient's brain by applying a stimulus to the brain, and at the same time, investigating a response, and the high-intensity focused ultrasound outputted from the second transducer
(Continued)

may be used to ablate or remove the detected lesion by applying a thermal or mechanical stimulus to the lesion.

4 Claims, 4 Drawing Sheets

(51) Int. Cl.
*A61B 8/08* (2006.01)
*A61N 7/02* (2006.01)

(52) U.S. Cl.
CPC ............ *A61B 8/4494* (2013.01); *A61B 8/461* (2013.01); *A61B 8/54* (2013.01); *A61N 7/02* (2013.01); *A61N 2007/003* (2013.01); *A61N 2007/0052* (2013.01)

(56) References Cited

U.S. PATENT DOCUMENTS

| | | | |
|---|---|---|---|
| 6,245,867 B1 * | 6/2001 | Debras | C08L 23/06 526/106 |
| 6,719,694 B2 * | 4/2004 | Weng | A61B 17/0057 310/336 |
| 7,211,044 B2 * | 5/2007 | Mast | A61B 8/08 600/439 |
| 8,696,581 B2 * | 4/2014 | Sverdlik | A61N 7/022 600/459 |
| 2003/0135084 A1 * | 7/2003 | Young | A61N 7/00 600/2 |
| 2005/0240126 A1 | 10/2005 | Foley et al. | |
| 2007/0088345 A1 * | 4/2007 | Larson | A61B 8/4438 606/27 |
| 2008/0177180 A1 | 7/2008 | Azhari et al. | |
| 2010/0009400 A1 * | 1/2010 | Glazer | G01N 33/5082 435/29 |
| 2011/0092781 A1 * | 4/2011 | Gertner | A61B 5/4035 600/301 |
| 2011/0112394 A1 | 5/2011 | Mishelevich | |
| 2012/0283502 A1 | 11/2012 | Mishelevich et al. | |
| 2013/0103028 A1 * | 4/2013 | Tsoref | A61N 7/022 606/41 |
| 2013/0144192 A1 | 6/2013 | Mischelevich et al. | |
| 2014/0194726 A1 | 7/2014 | Mishelevich et al. | |
| 2015/0258352 A1 * | 9/2015 | Lin | A61B 17/22004 601/2 |
| 2016/0236012 A1 * | 8/2016 | Zderic | A61B 5/14532 |
| 2017/0282215 A1 * | 10/2017 | Chaggares | G10K 11/355 |
| 2019/0038253 A1 | 2/2019 | Song et al. | |
| 2019/0175146 A1 * | 6/2019 | Lafon | A61B 8/08 |

FOREIGN PATENT DOCUMENTS

| | | | |
|---|---|---|---|
| KR | 10-2006-0121277 A | 11/2006 | |
| KR | 10-1533402 B1 | 7/2015 | |
| KR | 10-1625646 B1 | 5/2016 | |
| KR | 10-2017-0091813 A | 8/2017 | |
| KR | 10-1861842 B1 | 5/2018 | |
| WO | WO 2005/065408 A2 | 7/2005 | |
| WO | WO 2011/071703 A1 | 6/2011 | |
| WO | WO 2014/055906 A1 | 4/2014 | |
| WO | WO 2015/027164 A1 | 2/2015 | |
| WO | WO 2016/210133 A1 | 12/2016 | |
| WO | WO-2018037130 A1 * | 3/2018 | ............ A61B 8/469 |

OTHER PUBLICATIONS

J. Kennedy, "High-intensity focused ultrasound in the treatment of solid tumours," Nature Reviews Cancer, vol. 5, pp. 321-327, Mar. 2005 (Year: 2005).*
C. Maleke, et al., "Harmonic motion imaging for focused ultrasound (HMIFU): a fully integrated technique for sonication and monitoring of thermal ablation in tissues," Phys. Med. Biol., vol. 53, pp. 1773-1793, Mar. 2008 (Year: 2008).*
S. Kuang, et al., "Confocal dual-frequency enhances the damaging effect of high-intensity focused ultrasound in tissue-mimicking phantom," Minimally Invasive Therapy & Allied Technologies, vol. 17, No. 5, pp. 285-291, Oct. 2008 (Year: 2008).*
S. Guo, Y. Jing, X. Jiang, "Temperature rise in tissue ablation using multi-frequency ultrasound," IEEE Transactions Ultrasonics, Ferroelectrics, and Frequency Control, vol. 60, No. 8, pp. 1699-1707, Aug. 2013 (Year: 2013).*
K. Martin, B. Lindsey, J. Ma, M. Lee, S. Li, F. Foster, X. Jiang, and P. Dayton, "Dual-Frequency Piezoelectric Transducers for Contrast Enhanced Ultrasound Imaging," Sensors, vol. 14, No. 11, pp. 20825-20842, Nov. 2014 (Year: 2014).*
N. Ellens, et al., "Frequency considerations for deep ablation with high-intensity focused ultrasound: A simulation study," Medical Physics, vol. 42, No. 8, pp. 4896-4910, Jul. 2015 (Year: 2015).*
L. Deng, et al., "A multi-frequency sparse hemispherical ultrasound phased array for microbubble-mediated transcranial therapy and simultaneous cavitation mapping," Phys. Med. Biol., vol. 61, pp. 8476-8501, Nov. 2016 (Year: 2016).*
N. Nizam-Uddin, et al., "Enhanced Energy Localization in Hyperthermia Treatment Based on Hybrid Electromagnetic and Ultrasonic System: Proof of Concept with Numerical Simulations," BioMed Research International, pp. 1-18, Aug. 2017 (Year: 2017).*
B. A. Rabkin et al., "Involvement of cavitation in the appearance of hyperechoic regions in ultrasound image visualization of high intensity focused ultrasound therapy: in-vivo results," IEEE Ultrasonics Symposium, 2004 (Year: 2004).*
Owen et al., "In Vivo Evaluation of a Mechanically Oscillating Dual-Mode Applicator for Ultrasound Imaging and Thermal Ablation," IEEE Transactions on Biomedical Engineering, vol. 57, No. 1, pp. 80-92, Jan. 2010 (Year: 2010).*

* cited by examiner

HIGH-LOW INTENSITY FOCUSED ULTRASOUND TREATMENT APPARATUS

DESCRIPTION OF GOVERNMENT-SPONSORED RESEARCH

This study was supported by the Research-based Hospital Support Program (Development of non-invasive ultrasound based neural control and muscle rehabilitation systems, Project serial number: 1465026068) of Ministry of Health and Welfare, and supported by the Original Technology Development Program for Brain Science (Development of MRI based image induced brain stimulation control systems for Internet•Gaming addiction treatment, Project serial number: 1711058920) of Ministry of Science and ICT under the supervision of Korean Institute of Science and Technology.

CROSS-REFERENCE TO RELATED APPLICATION

This application claims priority to Korean Patent Application No. 10-2018-0064719, filed on Jun. 5, 2018, and all the benefits accruing therefrom under 35 U.S.C. § 119, the contents of which in its entirety are herein incorporated by reference.

BACKGROUND

1. Field

The present disclosure relates to a high-low intensity focused ultrasound treatment apparatus, and more particularly, to a hybrid high-low intensity focused ultrasound treatment apparatus for simultaneous lesion detection and removal.

2. Description of the Related Art

To conduct therapy that mitigates a patient's pain or stimulates neural cell in a specific human body part, a method that inserts electrodes into the patient's human body has been used, but there is a risk that the human body can be damaged by this physical invasion process.

Recently, ultrasound stimulation therapy that can stimulate an affected part without a physical invasion process is widely used. Ultrasound may be classified into High-intensity Focused Ultrasound (HIFU) and Low-intensity Focused Ultrasound (LIFU) according to acoustic intensity, and it is known that high-intensity focused ultrasound is used for direct treatment, for example, necrosis of human body tissues such as cancer cells, tumors and lesions, while low-intensity focused ultrasound can induce medical effects without necrotizing human body tissues.

The unit of ultrasound intensity is indicated by spatial-peak temporal-average intensity (Ispta) and spatial-peak pulse average intensity (Isppa) according to the Acoustic Output Measurement Standard for Diagnostic Ultrasound Equipment by American Institute for Ultrasound in Medicine and National Electronics Manufacturers Administration (NEMA).

The standard for the type of ultrasound is not yet explicitly defined, but in general, according to U.S. FDA standards and European Safety standards, "low intensity ultrasound" is ultrasound having the spatial-peak temporal-average intensity (Ispta) of less than 3 $W/cm^2$ and refers to ultrasound within a range in which the human body is not damaged, and ultrasound having the spatial-peak temporal-average intensity of 3 $W/cm^2$ or above may be classified as "high intensity ultrasound".

Recently, medical technology is used, which treats neurological disorders such as cognitive impairment, anxiety and depression in a non-invasive way using low-intensity focused ultrasound (LIFU), or removes lesions in a non-invasive way using high-intensity focused ultrasound (HIFU).

However, because such a method fails to locate a lesion such as a brain tumor in real time and immediately remove the lesion, surgical precision is low and it is impossible to accurately identify the boundary between the lesion and other tissue, and thus there is a risk of damage of a functionally important tissue that needs not to be incised.

SUMMARY

There is provided a hybrid high-low intensity focused ultrasound treatment apparatus designed to simultaneously output low-intensity focused ultrasound (LIFU) for detecting a lesion and high-intensity focused ultrasound (HIFU) for removing the detected lesion to increase the precision of non-invasive treatment and reduce danger.

Further, there is provided a means for monitoring if the lesion is being removed by high-intensity focused ultrasound in real time to further increase the precision of non-invasive treatment.

To achieve the above-described object, there are provided embodiments of a hybrid high-low intensity focused ultrasound treatment apparatus for simultaneous lesion detection and removal.

In an embodiment, the treatment apparatus includes a plurality of ultrasound sources, and a controller to control frequency and intensity of focused ultrasound outputted from the ultrasound sources, wherein each of the ultrasound sources includes a first ultrasound transducer to output low-intensity focused ultrasound to detect a lesion, and a second ultrasound transducer to output high-intensity focused ultrasound to ablate or remove the detected lesion.

In an embodiment, the low-intensity focused ultrasound outputted from the first ultrasound transducer may be used to detect a lesion in a patient's brain by applying a stimulus to the brain, and at the same time, investigating a response, and the high-intensity focused ultrasound outputted from the second ultrasound transducer may be used to ablate or remove the detected lesion by applying a thermal or mechanical stimulus to the lesion.

In an embodiment, the first ultrasound transducer may output the low-intensity focused ultrasound having a center frequency of 200 kHz to 1 MHz, and the second ultrasound transducer may output the high-intensity focused ultrasound having a center frequency of 200 kHz to 1 MHz, or 1 MHz or above.

In an embodiment, the first ultrasound transducer and the second ultrasound transducer may be formed in a shape of concentric circles sharing a target focal point.

In an embodiment, the treatment apparatus may further include an acoustic cavitation detector to monitor if the lesion is being ablated or removed by the high-intensity focused ultrasound.

In an embodiment, the acoustic cavitation detector may include a signal source to output a detection signal, and a signal receiver to receive an acoustic signal emitted from cavitation, and the treatment apparatus may further include an image processor 40 to process the cavitation detected by the acoustic cavitation detector into an image, and an image display unit 50 to output the image.

According to the embodiment of the present disclosure, a lesion in a patient's brain may be detected by delivering stimuli to the brain using low-intensity focused ultrasound (LIFU) and investigating responses, and at the same time, the lesion may be ablated or removed by delivering thermal or mechanical stimuli to the detected lesion using high-intensity focused ultrasound (HIFU).

As described above, it is possible to locate the lesion in real time and immediately remove the lesion, thereby increasing the precision and minimizing damage of a functionally important tissue that needs not to be incised.

In addition, acoustic cavitation that occurs during ultrasound exposure may be detected in real time, thereby further increasing the precision of non-invasive treatment.

DETAILED DESCRIPTION

Figure 1:
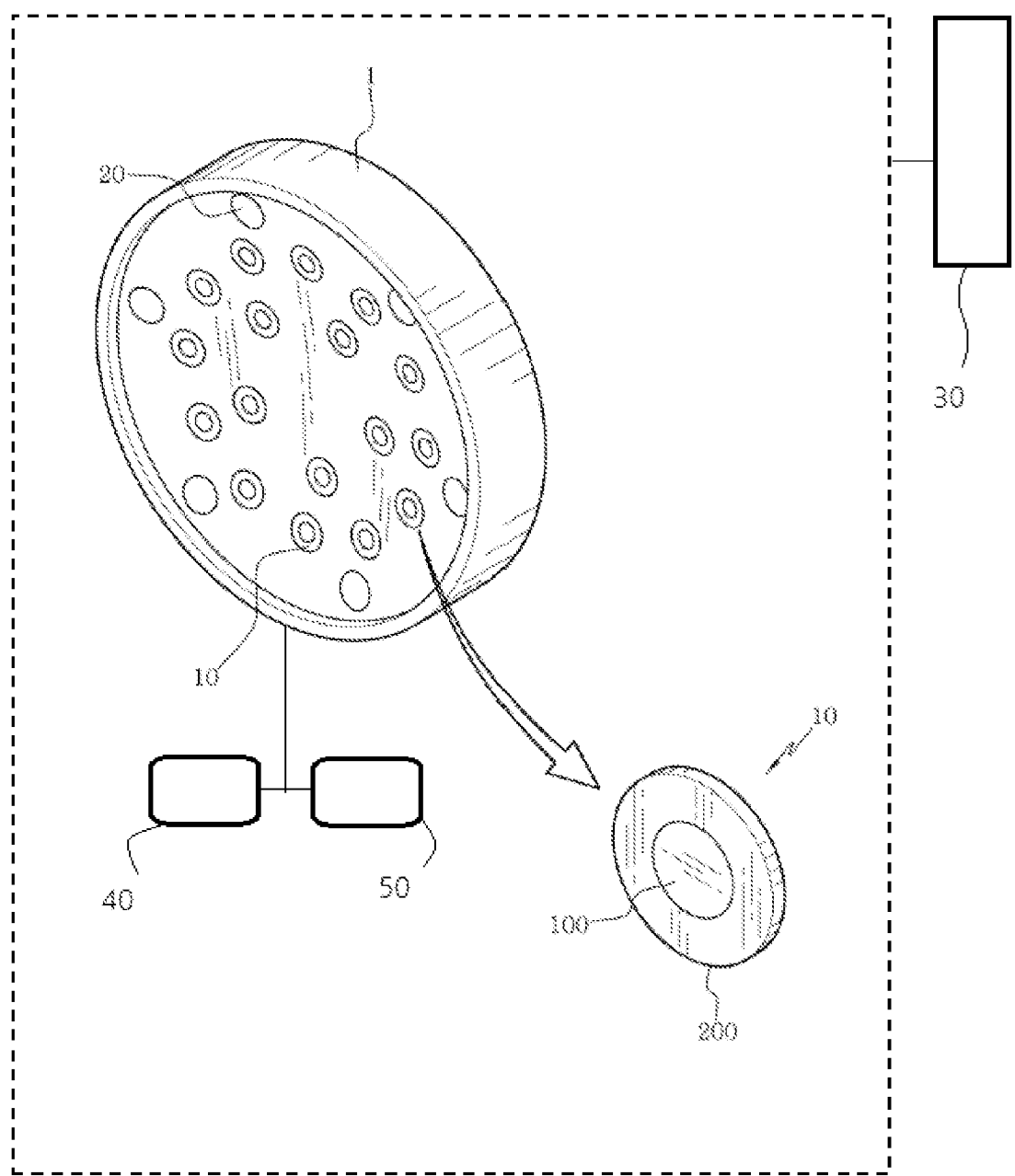
FIG. 1 is a diagram showing a high-low intensity focused ultrasound treatment apparatus according to an embodiment.

The following detailed description of the present disclosure is made with reference to the accompanying drawings, in which particular embodiments for practicing the present disclosure are shown for illustration purposes. These embodiments are described in sufficiently detail for those skilled in the art to practice the present disclosure. It should be understood that various embodiments of the present disclosure are different but do not need to be mutually exclusive. For example, particular shapes, structures and features described herein in connection with one embodiment can be embodied in other embodiment without departing from the spirit and scope of the present disclosure. It should be further understood that changes can be made to locations or arrangements of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote same or similar functions in many aspects.

Hereinafter, exemplary embodiments of a focused ultrasound stimulation apparatus will be described in more detail with reference to the accompanying drawings.

FIG. 1 is a diagram showing a high-low intensity focused ultrasound treatment apparatus according to an embodiment.

Referring to FIG. 1, the apparatus includes a body 1 and a plurality of ultrasound sources 10 and a plurality of acoustic cavitation detectors 20 included in the front surface of the body 1. The body 1 may include an electric circuit, a control circuit and a power supplier to supply power or control the power supply to each of the ultrasound sources 10 and the acoustic cavitation detectors 20, and an arm that freely moves may be attached to the rear surface of the body 1 to control the location of the body 1. The remaining additional mechanical/electronic components except the ultrasound sources 10 and the acoustic cavitation detectors 20 have a similar structure and principle to those used in a general ultrasound treatment apparatus, and its detailed description is omitted herein.

Each ultrasound source 10 includes one or more ultrasound transducers. The ultrasound transducer is a sound source that outputs ultrasound, and is designed to output low intensity ultrasound of 3 W/cm$^2$ (Ispta) or less and high intensity ultrasound of 3 W/cm$^2$ (Ispta) or above by adjusting the output according to a target region to treat and the purpose of treatment.

In general, the ultrasound transducer converts alternating current energy of 20 KHz or above to mechanical vibration of the same frequency by using the piezoelectric effect or the magnetostrictive effect. For example, the transducer may include a body that is open to one side and piezoelectric devices, and the body may be filled with air and each piezoelectric device may be connected to a wire to apply voltage. The piezoelectric device uses a material that produces the piezoelectric effect such as Quartz and Turmaline, and the transducer may generate and output ultrasound using the piezoelectric effect of the piezoelectric device. This structure of the transducer is provided for illustration purposes only, and the transducer is not limited to a particular structure or effect. The piezoelectric device of the transducer may output a suitable intensity of ultrasound by adjusting the output according to a target region to treat and the purpose of treatment, and the outputted ultrasound overlaps to form an ultrasound beam.

Referring to FIG. 1, each ultrasound source 10 may include a first ultrasound transducer 100 and a second ultrasound transducer 200 in the shape of concentric circles. The first ultrasound transducer 100 may output low-intensity focused ultrasound (LIFU) to detect a lesion in a patient's body such as a cancer cell or a tumor, and the second ultrasound transducer 200 may output high-intensity focused ultrasound (HIFU) to remove the detected lesion. When the first and second ultrasound transducers 100, 200 are formed in the shape of concentric circles as shown in FIG. 1, the first and second ultrasound transducers 100, 200 may be set to share a focal point, and may remove the detected lesion more accurately. Although FIG. 1 shows the concentric hybrid transducer, this is provided for illustration purposes only and the first and second ultrasound transducers 100, 200 may be formed in any shape for simultaneously or individually outputting high-low intensity focused ultrasound.

Figure 2A:
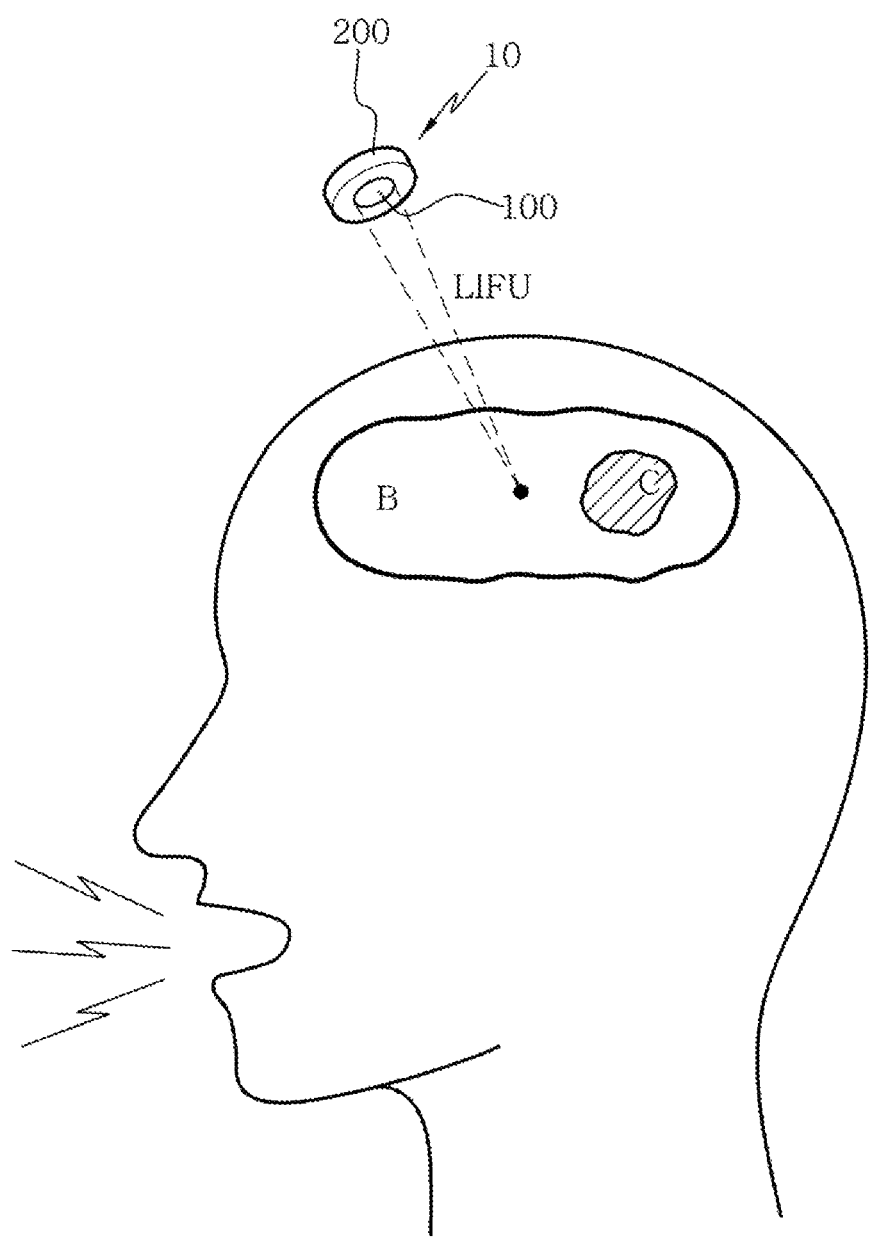
FIGS. 2A to 2C are diagrams showing a lesion detection and removal process using a high-low intensity focused ultrasound treatment apparatus according to an embodiment.
Figure 2B:
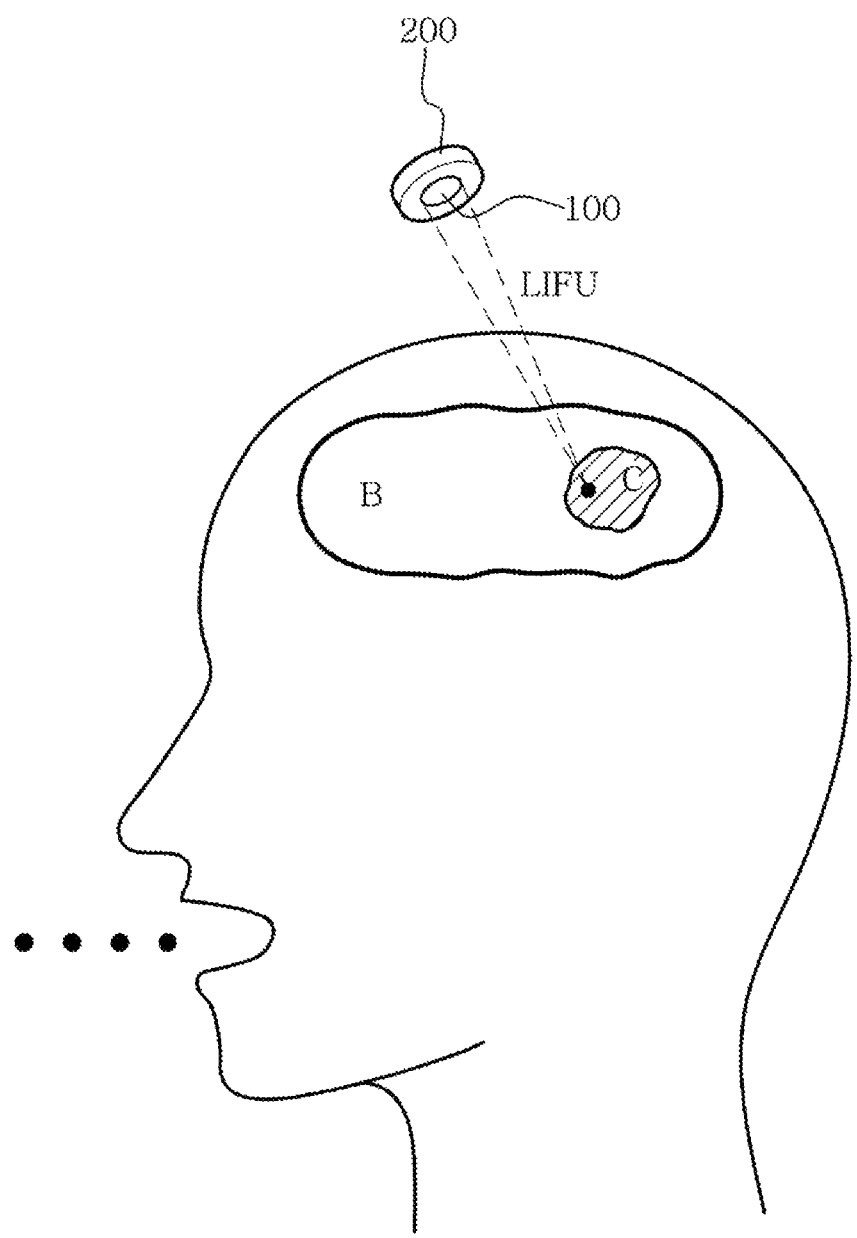
Figure 2C:
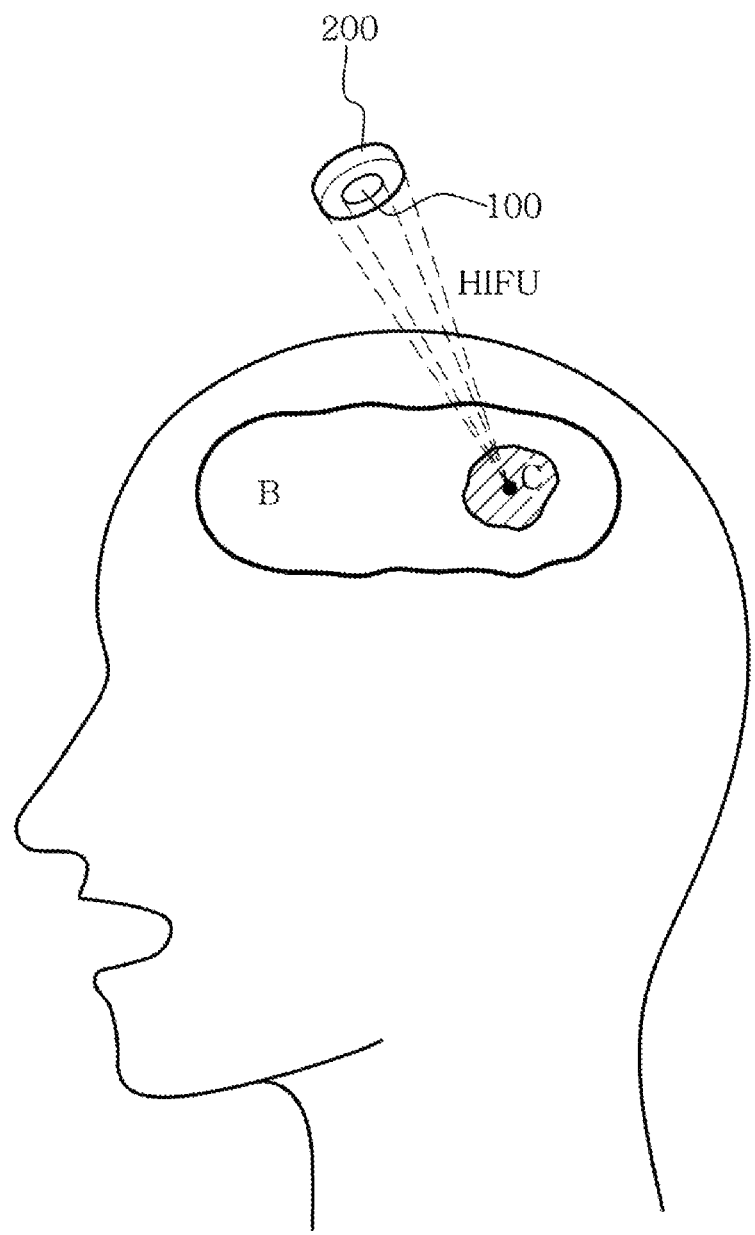

Referring to FIGS. 2A and 2B, an embodiment is shown, in which the lesion in the patient's brain is detected using low-intensity focused ultrasound (LIFU).

The human brain controls most of various functions of the body, and during a specific action or response, a specific brain area is activated, and in turn, when stimuli are delivered to a specific brain area, a specific body action or response may appear. On the contrary, when a specific brain area is damaged or has a tumor, even though stimuli are delivered to the corresponding part, a specific body response may not appear. Recently, many discoveries about the correlation between a specific brain area and a specific body response are made through brain mapping studies.

Using this principle, lesion detection has been performed by opening a patient's cranium, delivering electrical stimuli through electrodes and investigating if a body response corresponding to the corresponding area appears. For example, in the brain area involved in language functions, when stimuli are delivered to a normal brain tissue, the patient can speak, but when stimuli are delivered to a damaged area or an area having a tumor, the patient cannot speak, and through this, the corresponding part is determined to be abnormal.

In view of this principle, the present disclosure provides a non-invasive lesion detection method using low-intensity focused ultrasound (LIFU) to reduce the aftereffect and danger of the invasive examination and treatment process.

First, a user (for example, a person having a medical license or equivalent qualification) operates the treatment apparatus in a detection mode to detect a lesion in a patient's brain. In the detection mode, among the plurality of ultrasound sources 10, only the first ultrasound transducer 100 is activated, and only low-intensity focused ultrasound (LIFU) is outputted by the ultrasound transducer.

In an embodiment, low-intensity focused ultrasound (LIFU) has sufficient frequency to pass through the cranium (for example, having a center frequency of about 200 kHz to 1 MHz) and a proper intensity (for example, 3 W/cm$^2$ (Ispta) or less) to stimulate human tissues, but not damage. The user may arbitrarily control the detailed settings such as frequency or intensity of focused ultrasound through interfacing with the controller 30 included in the treatment apparatus. The controller may refer to devices and/or systems operating through processor units and/or circuits connected with computer.

As shown in FIG. 2A, when stimuli is applied to a normal brain tissue in the patient's brain area B using ultrasound, a corresponding body response appears. For example, when stimuli are delivered to a normal brain tissue in the brain area involved in language functions, the patient can speak. In this case, the user continues to scan by controlling the ultrasound irradiation direction (for example, moving using the arm attached to the rear surface of the body of the apparatus or electronically controlling the direction of the multi-array transducer) to find the lesion C.

As shown in FIG. 2B, when the focal point of low-intensity focused ultrasound (LIFU) reaches the lesion C such as cancer cell or tumor in the brain during scanning, a normal body response corresponding to the corresponding brain area does not appear. For example, if the brain area involved in language functions has a problem, even though stimuli are delivered to this area, the patient cannot speak, and from this, the user can identify that the lesion is present at the current focal point of focused ultrasound.

Subsequently, the user operates the treatment apparatus in a treatment mode to remove the detected lesion. In the treatment mode, the second ultrasound transducer 200 of the ultrasound sources 10 are activated together, and high-intensity focused ultrasound (HIFU) is outputted. In an embodiment, high-intensity focused ultrasound has sufficient intensity to remove the detected lesion such as tumor by applying thermal or mechanical stimuli to the lesion. For example, high-intensity focused ultrasound may be set to have a center frequency of 200 kHz to 1 MHz, or 1 MHz or above and the intensity of 3 W/cm$^2$ (Ispta) or above. The user may arbitrarily control the detailed settings such as changes in frequency, intensity and thermal/mechanical stimulation type of focused ultrasound through interfacing with the control unit included in the treatment apparatus.

The thermal stimulus burns the lesion with the gradually increasing temperature by irradiating an ultrasound beam onto the corresponding focal point, and the mechanical stimulus incises the body tissue by irradiating a continuous high intensity of ultrasound beam onto the corresponding focal point. This type of ultrasound attack is made by the medium of cavitation, making it possible to monitor a treatment situation in real time through acoustic cavitation detection technology as described below.

According to the above-described embodiment, the user can detect the lesion by scanning the patient's brain using low-intensity focused ultrasound (LIFU), and at the same time, immediately remove the detected lesion by irradiating high-intensity focused ultrasound (HIFU) to the same focal point. The operation method involving imaging the patient's brain structure beforehand through CT or MRI imaging and incising the tissue cannot achieve simultaneous examination and treatment, reducing the precision, and as a consequence, failing to accurately identify the boundary between the lesion and other tissue, and thus there is a risk of damage of a functionally important tissue that needs not to be incised, but according to the present disclosure, lesion detection and removal is simultaneously performed, and thus precision is very high and rapid treatment is achieved.

Referring back to FIG. 1, the high-low intensity focused ultrasound treatment apparatus may further include the acoustic cavitation detector 20 on the front surface of the body 1. The acoustic cavitation detector 20 is used to monitor if the lesion is being removed by high-intensity focused ultrasound (HIFU). As shown in FIG. 1, the plurality of acoustic cavitation detectors 20 may be disposed at suitable positions.

The cavitation refers to a phenomenon in which cavities are generated in a fluid where ultrasound travels when the pressure changes with a change in speed of the fluid. While ultrasound travels in the fluid, compression and rarefaction act in an alternating manner, and vacuum cavities are generated in the solution by rarefaction and instantaneously filled with dissolved gas and turn into bubbles.

When high-intensity focused ultrasound (HIFU) is continuously irradiated onto the target focal point, cavitation occurs and oscillation of resulting bubbles generates shear stress around the bubbles to produce shock, or when the pressure of the sound wave is relatively high, bubbles increase in size at a high rate and collapse by inertia to produce shock. That is, when all cavitation phenomena occur, shocks are produced from generation, oscillation and collapse of bubbles, and using this, lesions are removed with high-intensity focused ultrasound (HIFU) by destructing and incising body tissues, and this is the treatment principle.

The acoustic cavitation detector 20 monitors the thermal or mechanical stimuli applied to the lesion with high-intensity focused ultrasound (HIFU) in real time. In an embodiment, the passive acoustic mapping technique may be used, and may monitor the location and size of cavitation by transmitting a signal for cavitation detection using a signal source (for example, an ultrasound transducer) included in the acoustic cavitation detector 20, and receiving a reflected signal of the detection signal caused by cavitation through a signal receiver (for example, an imaging probe).

A more accurate monitoring method may use the active cavitation mapping technique, and monitor the location and size of cavitation by calculating an amplitude difference between an image signal of the patient's brain structure and a signal for detection. A variety of other cavitation detection methods may be performed, and the present disclosure is not limited to a particular method.

In an embodiment, the high-low intensity focused ultrasound treatment apparatus may further include an image processing unit (not shown) to process the cavitation by the acoustic cavitation detector 20 into an image, and an image output unit (not shown) to output the image, such as display devices. Using this configuration, the user may perform a therapeutic operation while monitoring the cavitation area, that is, if the lesion is being removed by high-intensity focused ultrasound (HIFU) in real time, thereby further increasing the precision of non-invasive ultrasound treatment.

While the present disclosure has been hereinabove described with reference to the embodiments shown in the drawings, this is provided for illustration purposes only and those skilled in the art will understand that various modifications and variations may be made thereto. However, it should be noted that such modifications fall in the technical protection scope of the present disclosure. Accordingly, the true technical protection scope of the present disclosure should be defined by the technical spirit of the appended claims.

What is claimed is:

1. A high-low intensity focused ultrasound treatment apparatus for simultaneous lesion detection and removal, the treatment apparatus comprising:
    a plurality of ultrasound sources;
    a controller to control a frequency and an intensity of focused ultrasound outputted from the plurality of ultrasound sources; and
    an acoustic cavitation detector to monitor if a lesion is being ablated or removed by high-intensity focused ultrasound,
    wherein each of the plurality of ultrasound sources comprises:
        a first ultrasound transducer to output low-intensity focused ultrasound to detect the lesion, wherein the low-intensity focused ultrasound is used to detect the lesion by applying a stimulus to body parts, and at the same time, investigating a response; and
        a second ultrasound transducer to output the high-intensity focused ultrasound to ablate or remove the detected lesion by applying a thermal or mechanical stimulus to the detected lesion,
    wherein the first ultrasound transducer and the second ultrasound transducer are formed in a shape of concentric circles sharing a target focal point, the first ultrasound transducer being formed at a center of the ultrasound source and the second ultrasound transducer being formed in an annular ring around the first ultrasound transducer,
    wherein, in a detection mode to detect the lesion, only the first ultrasound transducer is activated, and only the low-intensity focused ultrasound is outputted, and
    wherein, in a treatment mode to ablate or remove the lesion, the second ultrasound transducer is activated together with the first ultrasound transducer, and the high-intensity focused ultrasound is outputted.

2. The high-low intensity focused ultrasound treatment apparatus according to claim 1, wherein the first ultrasound transducer outputs the low-intensity focused ultrasound having a center frequency of 200 kHz to 1 MHz, and
    wherein the second ultrasound transducer outputs the high-intensity focused ultrasound having a center frequency of 200 kHz to 1 MHz, or 1 MHz or above.

3. The high-low intensity focused ultrasound treatment apparatus according to claim 1,
    wherein the treatment apparatus further comprises:
        an image processor to process the cavitation detected by the acoustic cavitation detector into an image; and
        an image display unit to output the image.

4. The high-low intensity focused ultrasound treatment apparatus according to claim 1, wherein the first ultrasound transducer outputs the low-intensity focused ultrasound having a low intensity of 3 $W/cm^2$ (Ispta) or less, and
    wherein the second ultrasound transducer outputs the high-intensity focused ultrasound having a high intensity of 3 $W/cm^2$ (Ispta) or above.

* * * * *